US012784920B2

(12) United States Patent
Wright

(10) Patent No.: US 12,784,920 B2
(45) Date of Patent: Nov. 3, 2026

(54) WELLNESS SYSTEM

(71) Applicant: Green Line Business Group, LLC, Newark, DE (US)

(72) Inventor: Anthony D. Wright, Wilmington, DE (US)

(73) Assignee: Green Line Business Group LLC, Newark, DE (US)

( * ) Notice: Subject to any disclaimer, the term of this patent is extended or adjusted under 35 U.S.C. 154(b) by 17 days.

(21) Appl. No.: 18/555,118

(22) PCT Filed: Apr. 13, 2022

(86) PCT No.: PCT/US2022/024529
§ 371 (c)(1),
(2) Date: Oct. 12, 2023

(87) PCT Pub. No.: WO2022/221358
PCT Pub. Date: Oct. 20, 2022

(65) Prior Publication Data

US 2024/0203607 A1 Jun. 20, 2024

Related U.S. Application Data

(60) Provisional application No. 63/175,399, filed on Apr. 15, 2021.

(51) Int. Cl.
*G16H 80/00* (2018.01)
*A61B 5/00* (2006.01)
(Continued)

(52) U.S. Cl.
CPC ........... *G16H 80/00* (2018.01); *A61B 5/7465* (2013.01); *G16H 20/10* (2018.01); *G16H 40/67* (2018.01)

(58) Field of Classification Search
CPC ........ G16H 80/00; G16H 20/10; G16H 40/67; G16H 10/20; G16H 40/20; G16H 50/20;
(Continued)

(56) References Cited

U.S. PATENT DOCUMENTS 6,269,339 B1 7/2001 Silver
2014/0032234 A1 * 1/2014 Anderson ............ A61B 5/0022 600/595

(Continued)

FOREIGN PATENT DOCUMENTS

WO WO-2015059306 A1 * 4/2015 ............. G16H 15/00

OTHER PUBLICATIONS

EveryDose, Meet EveryDose's Medication Adherence Platform, https://www.everydose.ai/news-and-blog/clinician-tips/meet-everydoses-medication-adherence-platform/ (Year: 2020).*

(Continued)

*Primary Examiner* — Joy Chng
(74) *Attorney, Agent, or Firm* — Devlin Law Firm LLC

(57) ABSTRACT

A wellness system provides a low-cost healthcare solution and interactive interface that enables anyone with a computer or smartphone to take control of their own health by quickly being connected with a doctor, being diagnosed, having medications prescribed, being connected with support groups and quickly having access to statics regarding their health as well as current publications and research on conditions and treatment methods. The exemplary wellness system provides a low-cost health care alternative without expensive insurance, complicated insurance forms, and reduces the need for lengthy, inconvenient office visits. The system requires no health insurance and is intended for ongoing wellness maintenance and non-emergency care that might otherwise be resolved with a problematic office visit. Health data may be input to the system including health data
(Continued)

from a sensor and these health data may be monitored by a healthcare professional.

7 Claims, 5 Drawing Sheets

(51) Int. Cl.
*G16H 20/10* (2018.01)
*G16H 40/67* (2018.01)

(58) Field of Classification Search
CPC ...... G16H 70/20; G16H 10/60; A61B 5/7465; A61B 5/0022; A61B 5/01; A61B 5/021; A61B 5/024; A61B 5/14532; A61B 5/6898
USPC .......................................................... 705/2–3
See application file for complete search history.

(56) References Cited

U.S. PATENT DOCUMENTS

| | | | | |
|---|---|---|---|---|
| 2014/0236759 | A1 | 8/2014 | Mirabile | |
| 2018/0197260 | A1 * | 7/2018 | Stollman | G16H 40/67 |
| 2019/0355482 | A1 * | 11/2019 | Taneja | H04L 67/1097 |
| 2020/0402662 | A1 * | 12/2020 | Esmailian | G16H 50/70 |

OTHER PUBLICATIONS

Da Silva et al. "Commercial Devices-Based System Designed to Improve the Treatment Adherence of Hypertensive Patients." Sensors (Basel, Switzerland) vol. 19,20 4539. Oct. 18, 2019, doi: 10.3390/s19204539 (Year: 2019).*
International Search Report for PCT/US2022/024529, issued Jun. 28, 2022.
Written Opinion for PCT/US2022/024529, issued Jun. 28, 2022.

* cited by examiner

WELLNESS SYSTEM

CROSS REFERENCE TO RELATED APPLICATIONS

This application claims the benefit of priority to U.S. provisional patent application No. 63/175,399, filed on Apr. 15, 2021; the entirety of which is hereby incorporated by reference herein.

BACKGROUND OF THE INVENTION

Same or Different Doctor

Field of the Invention

The invention relates to a wellness system that provides a low-cost healthcare solution and interactive interface that enables anyone with a computer or smartphone to take control of their own health by quickly being connected with a doctor, being diagnosed, having medications prescribed, being connected with support groups and quickly having access to statics regarding their health as well as current publications and research on conditions and treatment methods.

BACKGROUND

It is very difficult for many people to identify the correct doctors for their healthcare and wellness needs. They often schedule a first appointment only to find out that they need to schedule an appointment with another doctor, a specialist in many cases. In addition, some people do not have transportation and this makes it difficult for them to get to a medical facility or doctor's office or to a pharmacy to pick up medications.

SUMMARY OF THE INVENTION

The invention is directed to a wellness system that provides a low-cost healthcare solution and interactive interface that enables anyone with a computer or smartphone to take control of their own health by quickly being connected with a doctor, being diagnosed, having medications prescribed, being connected with support groups and quickly having access to statics regarding their health as well as current publications and research on conditions and treatment methods. The exemplary wellness system provides a low-cost health care alternative without expensive insurance, complicated insurance forms, and reduces the need for lengthy, inconvenient office visits." The system requires no health insurance at all, and is intended for ongoing wellness maintenance and non-emergency care that might otherwise be resolved with a problematic office visit.

A subscriber may log into the wellness system through a website or an App on their portable electronic device, such as a smartphone or tablet computer and provide health data, or symptoms or report an injury. A healthcare professional will be assigned through the wellness system and review the input and promptly provide feedback to the subscriber. The feedback may be a diagnosis, a request for more information about the condition or injury, a video call request, etc. Upon diagnosis by the healthcare professional, a treatment and/or medication will be prescribed.

The system decreases the need for in-person doctor visits, thereby saving time and money. The interactive system enables a person to provide health data input regarding their health status or condition using phone calls, text messaging, pictures, video and/or video calls with a healthcare professional, and senor input, such as blood pressure, or insulin levels. A wellness medical professional reviews the health data input on a consistent basis, such as daily, weekly or monthly or within 24 hours for urgent care. The wellness system reduces or eliminates the need for in-person appointments with healthcare professional or pharmacies. That means, reduced or eliminated need for transportation to a medical facility and no crowded waiting rooms, wherein infectious diseases can be spread, such as Covid 19. In addition, the wellness system may be provided at a low cost, thereby eliminating the need for insurance.

A subscriber to the wellness system may submit a text through their smartphone about a change or update to their heath status. This health data input will be reviewed by a healthcare professional and if any further data is required, additional information may be requested for input to the system. Any confidential information may be provided to the wellness system through secure means and may be encrypted or require a secure password.

For example, a person may have a cut and they may submit a picture to the wellness system. A medical professional may then provide instructions for cleaning and bandaging of the wound and they may request that a picture be uploaded each day to monitor healing. If the wound heals, then no additional treatment will be required. If however, the wound appears to be infected, such as by becoming red and swollen or by the presence of puss, the medical professional may order an antibiotic cream for application to the wound. The medication may be sent directly to the subscriber's home and instructions may be provided through the wellness system to the subscriber's smartphone for application. The subscriber may continue to submit pictures to the wellness system for review and monitoring.

In another example, a person may have high blood pressure and may submit their blood pressure on a daily basis, as health data input, to the wellness system. A medical professional may monitor the blood pressure and prescribe changes in blood pressure medication as required to keep the blood pressure in a safe range for the subscriber. A blood pressure cuff may be coupled with the subscriber's smartphone or other electronic interface device to enable uploading the data to the wellness system. Any number of health data sensors may provide data to a subscribers interactive electronic device, such as a smartphone, for submission to the wellness system including, but not limited to, a blood sugar monitor or sensor, a blood pressure sensor, a heart rate sensor, an oxygen level sensor, a urine composition sensor, a body temperature sensor, a sleep apnea sensor and the like.

Health data input may be input via text, voice message, picture, video and by interaction with a medical profession through a phone call or video call. The health data input may be provided through an interactive electronic device, such as a smartphone, that interfaces with the wellness website through an App. A subscriber may call and leave phone messages and a medical profession may return calls as required.

An exemplary wellness system website may be coupled with a database for storing subscribers health data input for review and for comparison over time. The database may have the required security measures to protect the subscriber's privacy regarding their wellness. An exemplary wellness system may operate through mobile phones and tablet computers that operate an App, as this may provide better security of personal and medical information.

An exemplary wellness system has polls or data that people can review regarding a particular condition. They can quickly find data and polling data regarding a treatment regime or feedback on doctors in their area. The system may provide links or data from their database on various conditions, the prognosis and most used treatments, such as medications, or surgical interventions.

An exemplary wellness system has information about medications including, but not limited to, recommended dosages, side effects, clinical effectiveness, study results and the like. A subscriber may review information about a medication prior to deciding that the medication is right for them; they can weigh the pros and cons.

An exemplary wellness system may have links to support groups and organization focused on a particular condition. A virtual support group may be provided for various conditions and the subscriber may choose to join anonymously and just view the support group meeting or they may choose to participate and provide their input to the group and/or ask questions of the group. The support group may be a telephonic or a video support group.

A healthcare professional or provider, as used herein may be a doctor, nurse, nurse practitioner, dentist, dental hygienist and the like.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 1 shows an exemplary interactive electronic device running a wellness system software app having a number of tabs for a subscriber to interface with.

Figure 1:
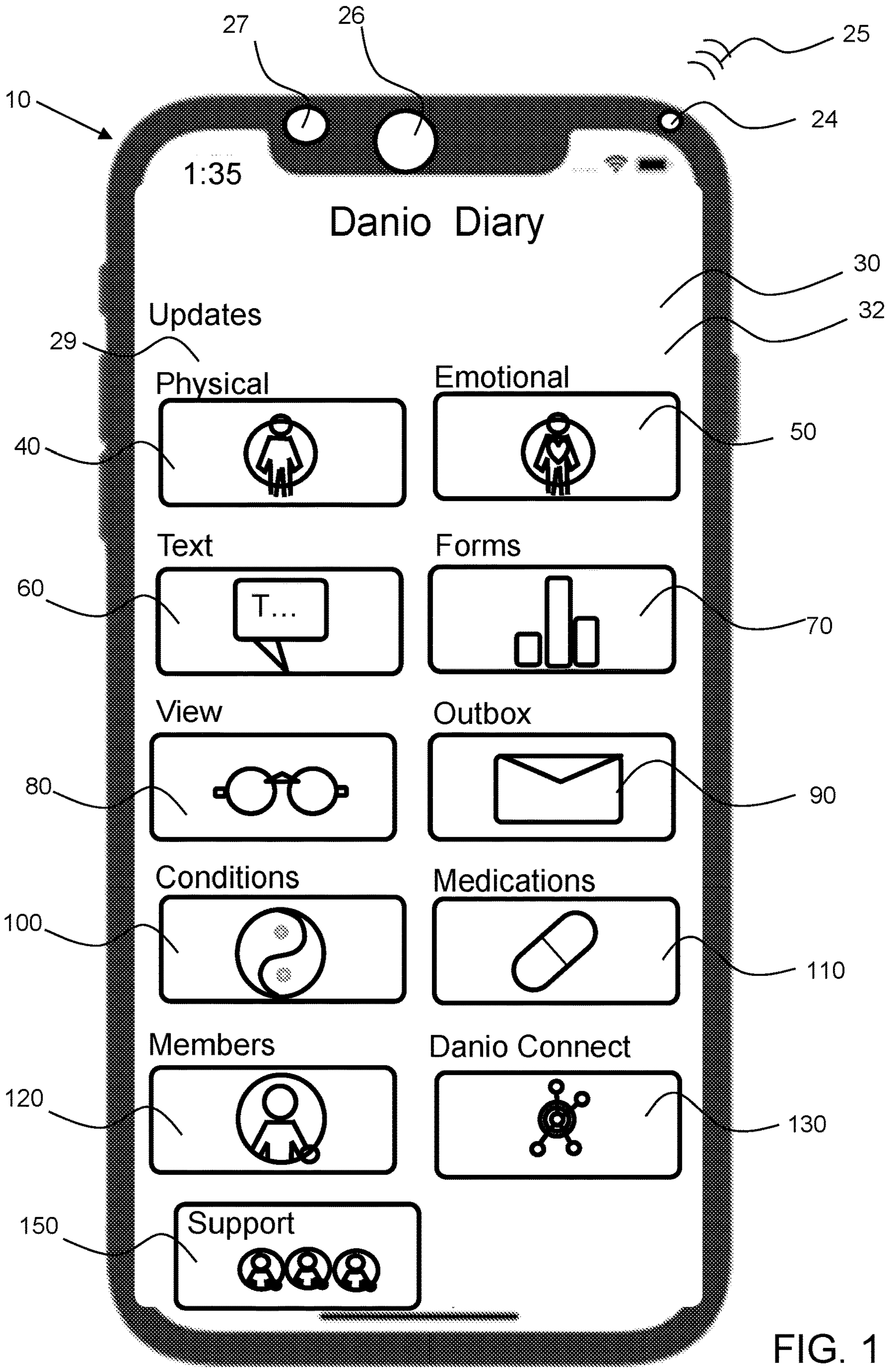

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to understood that where possible, features and components from one figure may be an included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary wellness system 10, employs an interactive electronic device 20, a smartphone 22, to run a wellness system software 30 such as a software App 32, that has a number of tabs for a subscriber to interface with.

A subscriber may click on the physical tab 40 to input health data regarding a physical condition or injury. When clicking on the tab, an icon of a person may be provided and the subscriber may click on an affected body part that they want to provide health data input for. For example, the person may click on a left knee and then additional tabs of input fields may be provided for inputting health data. There may be tabs or input fields for different conditions that may enable submission for an ongoing physical condition or injury.

Likewise, a subscriber may click on the emotional tab 50 to input health data regarding an emotional condition. When clicking on the emotional tab, a number of facial expression icons may be provided with different emotional states, such as depression, anxiety, manic and the like. A subscriber may click on the appropriate emotional state icon and then input additional information regarding their condition or health state. A medical professional may request input daily on their emotional state and the system may provide a quick rating questionnaire for the subscriber to fill out. A medical professional may review the input as required to provide treatment which may include medication or changes in medication dosages or types.

Health data input may be provided through text such as using a user input 29, such as the touchscreen to type in information about their condition, a microphone 28 to leave a message with health data or to speak with a healthcare professional, or a camera 26 to take pictures or video of a physical condition. The camera, microphone and speaker 27 may be used during a video call with a health care professional. A user input may be a keyboard coupled, physically or wirelessly with an interactive electronic device 20, which may be computer, laptop computer, or tablet computer, for example.

A subscriber may click on the text tab 60 to input text to the system with a particular question or concern. This may be a general purpose communication feature for subscribers. Questions about the system or about billing may be provided through the text tab. An administrator of the wellness system will respond quickly to the subscriber's inquiry.

A subscriber may click on forms tab 70 to access forms that may be required for a physical of emotional health data input. For example, a form for submission of blood glucose level may be found and filled out for submission.

A subscriber may click on view tab 80 to view their current wellness summary including medication and dosages prescribed. A subscriber may clear conditions from a list as they are treated and resolved. Likewise, they may clear medications from a list of medications as they are completed. This tab may be used to manage a listing of conditions for a subscriber.

A subscriber may click on the outbox tab 90 to see items in the outbox that have not yet been submitted. Health data input may be located in the outbox and saved prior to submission. In some cases, health data may be moved to the outbox after input and then subsequently submitted either automatically after some time, to aid in uploading speed, or manually by a subscriber.

A subscriber may click on the conditions tab 100 to view their current conditions. The view tab may allow changing of this list of conditions. The tab may also show the currently assigned healthcare professional assigned to this condition and may enable messaging or communication with the wellness system or healthcare professional.

A subscriber may click on the medications tab 110 to review a list of medications that have been prescribed along with the dosing regimen including amount, and intervals, such as time of day. The system may provide alerts as to when a prescription is due to be taken. This may be automatically generated based on the dosing regimen. The mobile device may call them with a reminder voice mail, or send a text that requires a reply for confirmation that the medication has been taken. The text might say, 200 mg ibuprofen, reply Y when taken. If no reply is received within a period of time, the system may keep track of this and may modify the dosing regimen as a result of a missed dose, or provide information on what to do as a result of missing a dose.

A subscriber may click on the members tab 120 to see a list of authorized members that have access to some or all of their wellness system data and conditions. An elderly person may list their son or daughter, for example, and they may monitor their mother's wellness and may provide additional input for a condition when necessary. In addition, the wellness system may alert one or more of the authorized members when a medication is missed. This way, a loved one can call and provide a friendly reminder to take the medication or may stop by to ensure medication regimens are followed. The authorized member may receive the medication notification as well on in lieu of the subscriber, and this may be an option when the two live together, thereby eliminating the need for the subscriber to receive medication notifications.

A subscriber may click on the *Danio* Connect tab 130 to connect with support groups and organizations for conditions or injuries. This tab may have information or links to information regarding conditions or injuries. The most recent publications from organizations may be provided, for example.

Figure 2:
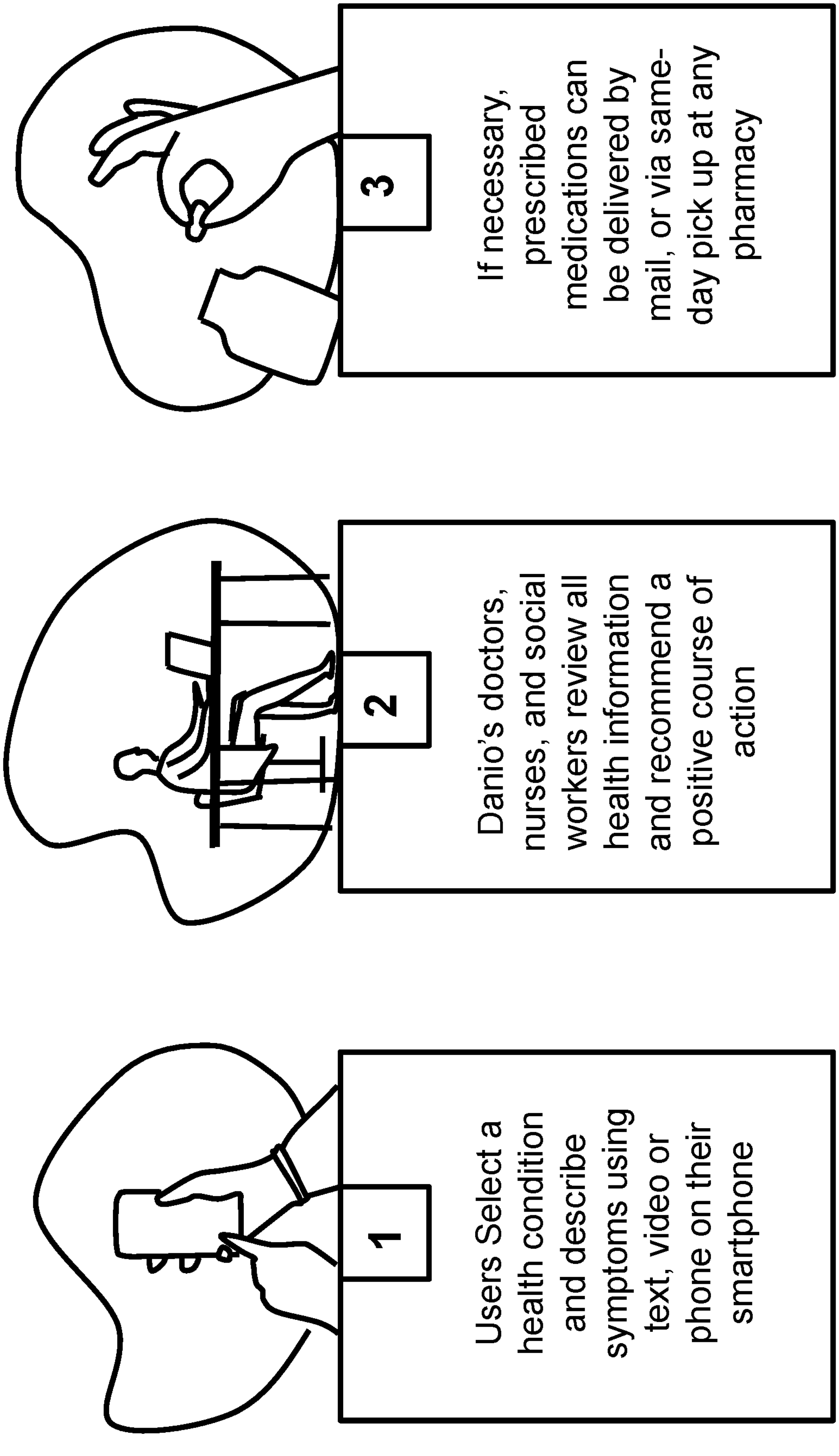
FIG. 2 shows a schematic for a subscriber to provide health data to the wellness system.

A subscriber may click on the support tab 150 to find support groups and organizations that may be associated with a condition or injury. The support groups may be a subscriber support group made up of subscribers, and/or members. A member support group for Alzheimer's may provide much needed support for family members with a loved one having Alzheimer's. The support group may be external however and may provide a quick means to find contact information for local organizations and groups. T FIG. 2 shows a schematic for a subscriber to provide health data to the wellness system. In "1" the user inputs health data to the wellness system. In "2" the healthcare professional reviews the health data and recommends a positive course of action, including physical therapy, medication(s), instructions to meet with a local doctor or other healthcare professional. In "3" medication has been prescribed and are delivered to the subscriber's home, or are made available at a pharmacy for pick-up.

Figure 3:
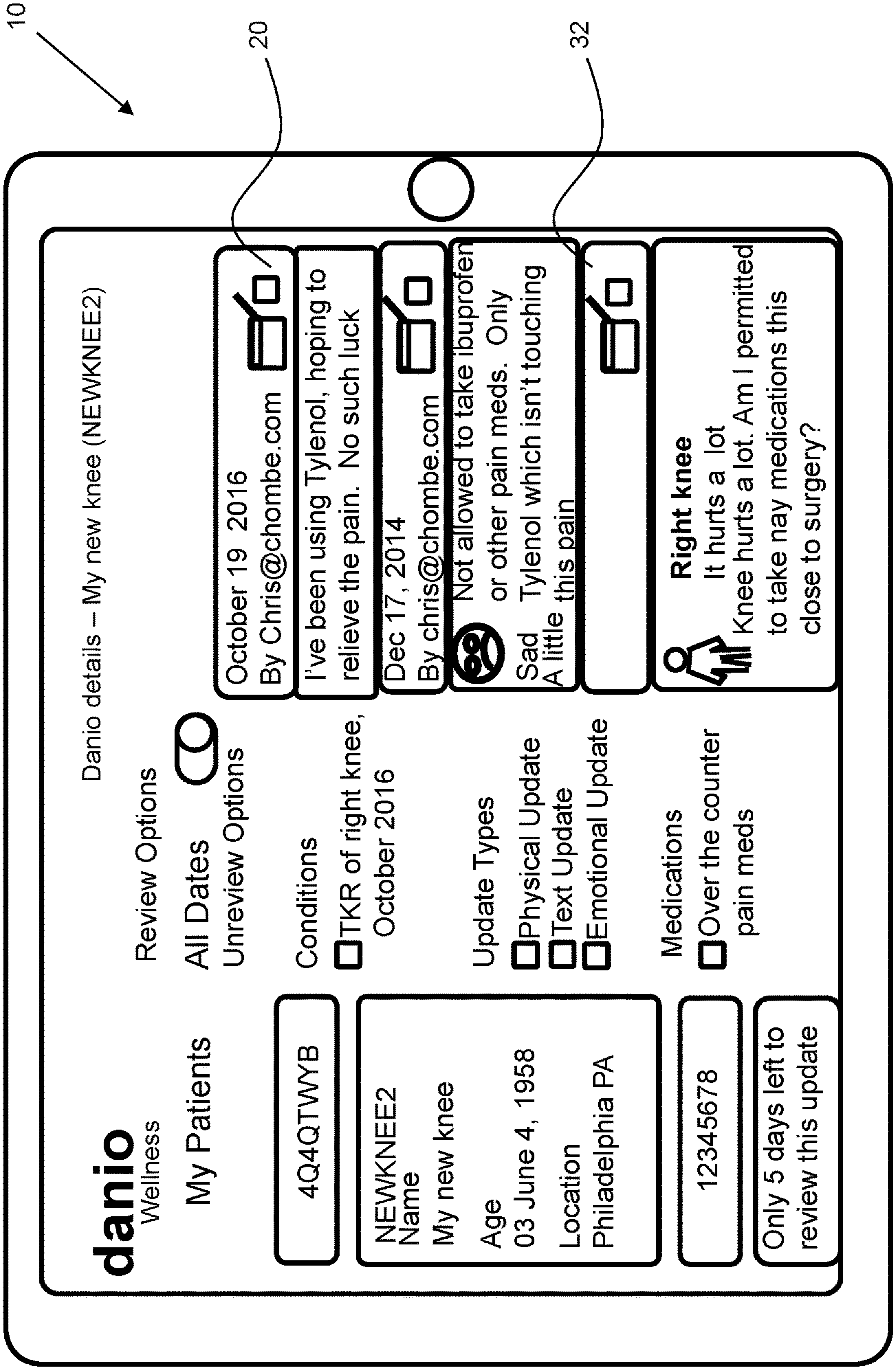
FIG. 3 shows an exemplary interactive electronic device running a wellness system software app and a healthcare professional's page with a subscriber patient's health data and current status.

As shown in FIG. 3, an exemplary wellness system 10 in operating on an interactive electronic device 20, a tablet computer, and is running a wellness system software app 32 with a healthcare professionals page with a subscriber patient's health data and current status. The healthcare professional may open up the subscriber page that shows any new health data input to the system and they may use this page to provide a course of action or change in a previous prescribed course of action. This page may allow a healthcare professional to access medical histories for a subscriber, review health status and updates, prioritize urgent requests, view prior progress notes, consult with physicians or other healthcare professionals, review electronic second opinions and communicate recommendations to members. The healthcare professional may provide diagnosis and prescribe medications or lab work through this page and may clear off actions as they are completed.

Figure 4:
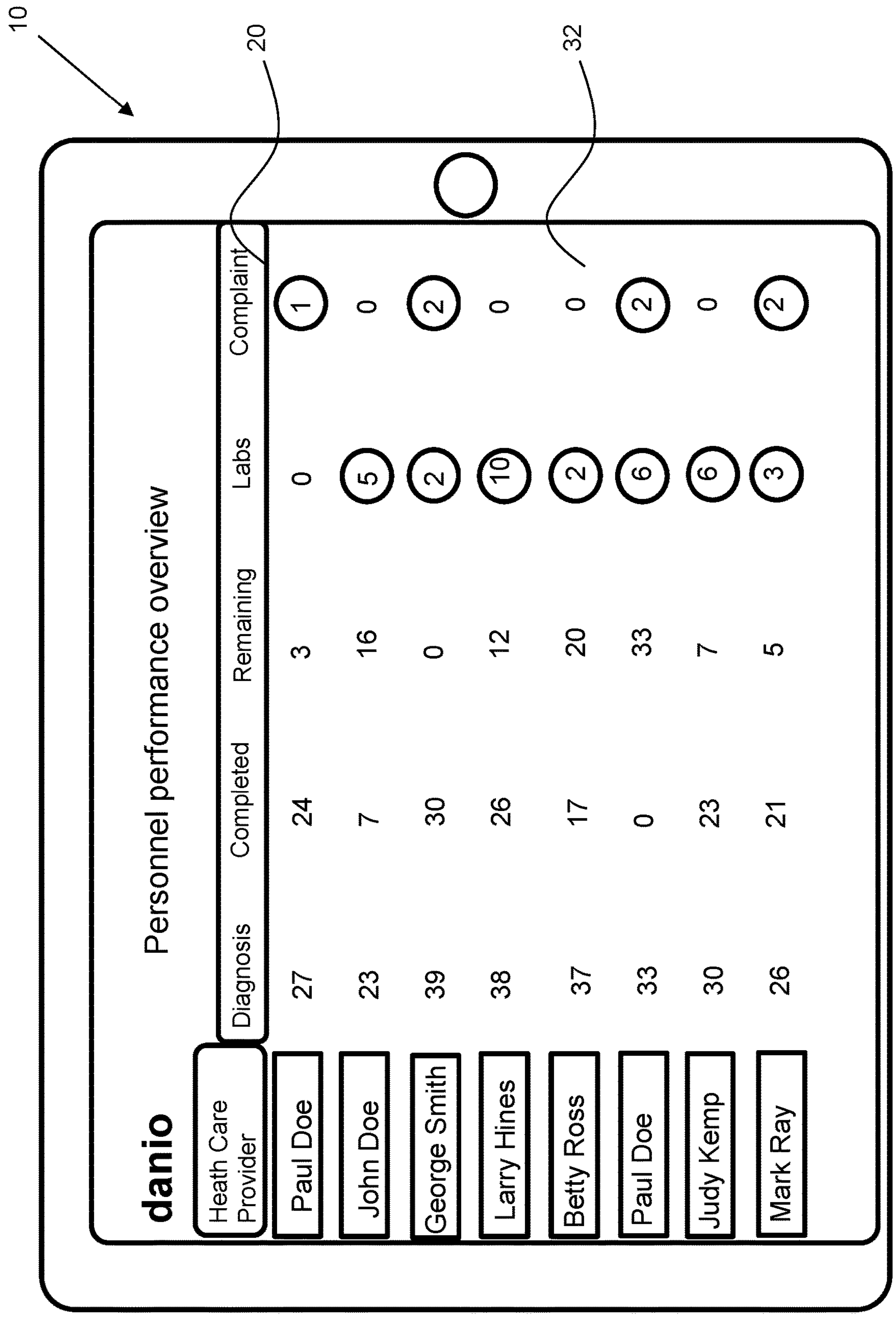
FIG. 4 shows an exemplary interactive electronic device running a wellness system software app and a healthcare professional performance summary.

As shown in FIG. 4, an exemplary wellness system 10 in operating on an interactive electronic device 20, a tablet computer, and is running a wellness system software app and a healthcare professionals performance summary. A wellness system administrator or manager may review healthcare professional's responsiveness and feedback from subscribers to ensure a high standard of care. The page may show a table with a list of healthcare professionals, or providers and the number of diagnosis they have submitted, how many they have completed, any remaining or open cases, how many labs they have out or are waiting for, and then number of complaints. This page may enable an administrator to manage healthcare teams, ensure accountability and timely reviews, scoreboard of productivity and responsiveness, manage and assign workload, evaluate the quality of care, review customer feedback, and chat and communicate with healthcare professionals about their subscribers they are treating.

Figure 5:
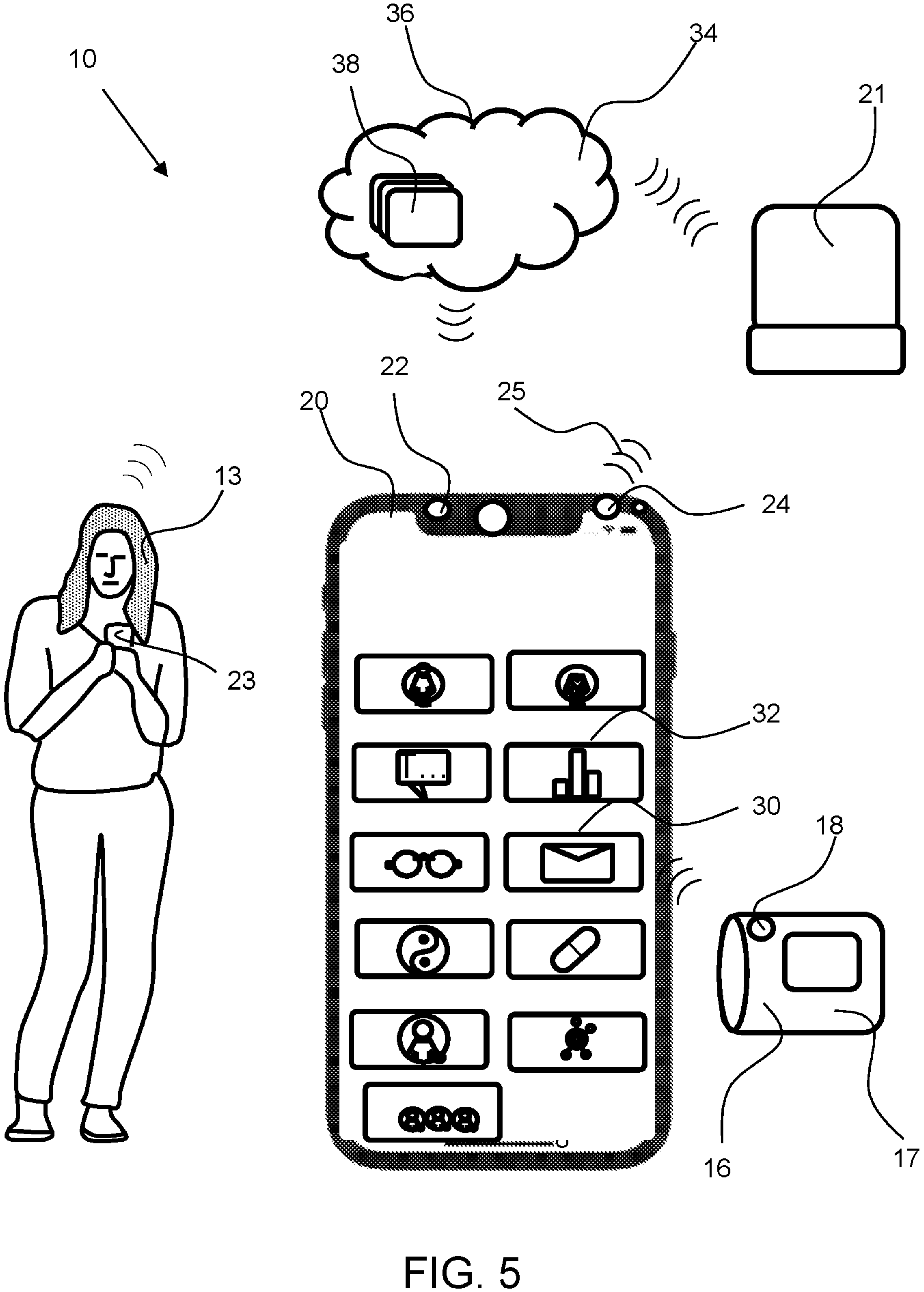
FIG. 5 shows a diagram of an exemplary wellness system having an interactive electronic device for a subscriber, a website that is accessed through the internet, an administrator interactive electronic device and a healthcare professional interactive electronic device and a sensor for obtaining heath data that is delivered to the wellness system.

As shown in FIG. 5, an exemplary wellness system 10 has an interactive electronic device 20 for a subscriber, a website 34 that is accessed through the internet 36, an administrator interactive electronic device 21 and a healthcare professional interactive electronic device 23. A blood pressure cup 17, an example of a health data input sensor 16 is configured to send health data input to the wellness system, such as through a wireless signal from a transmitter 18, or a wired connection to the subscriber's interactive electronic device 20. The wireless signal may be sent via a short range wireless signal, Bluetooth, to the subscriber interactive electronic device 20 or directly to the database 38 that is accessed by the wellness system 10.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A wellness system that comprises:

a) a database;

b) a system software that interfaces with said database;

c) a subscriber interactive electronic device that operates at least a portion of said system software;
  wherein the subscriber interactive electronic device is a mobile phone;
  wherein a subscriber inputs health data through the subscriber interactive electronic device to the database;

d) a treatment regimen that is received by said subscriber through said subscriber interactive electronic device;
  wherein the treatment regimen includes a dosing regimen;

e) a health data input sensor that measures health data of said subscriber;
  wherein the health data input sensor comprises a blood pressure sensor or a blood glucose sensor; and
  wherein the system software produces an alert on said subscriber interactive electronic device when a dose of a dosing regimen is due;

f) a member interactive electronic device that operates at least a portion of said system software; and
  wherein a member is selected by said subscriber on the subscriber interactive electronic device to have access to the subscriber's health data through the member interactive electronic device;
  wherein the system software produces an alert on said member interactive electronic device when a dose of the dosing regimen is due for said subscriber; and
  wherein the system software is configured to receive a confirmation input from the subscriber interactive device to confirm that said dose of the dosing regimen has been taken;
  wherein the system software modifies the dosing regimen based upon:
    (i) failure to receive the confirmation input from the subscriber interactive device within a predetermined period of time; and
    (ii) health data measured by the health data input sensor;
  wherein the modified dosing regimen is automatically transmitted to both the subscriber interactive electronic device and the member interactive electronic device; and
  wherein the system software generates a second member alert to a second member interactive electronic device when the confirmation input is not received within the predetermined period of time;
  wherein the health data measured by the health data input sensor is provided to the member interactive electronic device;
  wherein the health data input sensor provides the health data to the subscriber interactive electronic device;
  wherein the health data from the health data input sensor is automatically input to the subscriber interactive electronic device; and wherein the treatment regimen includes a prescribed medication with a dose regimen.

2. The wellness system of claim 1, wherein the health data input sensor is a blood glucose sensor.

3. The wellness system of claim 1, wherein the health data input sensor is a blood pressure sensor.

4. The wellness system of claim 1, wherein the health data input sensor further comprises a is a thermometer.

5. The wellness system of claim 1, wherein the health data input sensor further comprises a is a heart rate sensor.

6. The wellness system of claim 1, wherein the health data from the health data input sensor is automatically input to database through a wireless transceiver.

7. The wellness system of claim 1, wherein the at least a portion of said system software operating on the subscriber interactive electronic device is an App.

* * * * *